United States Patent
Taha et al.

(10) Patent No.: US 10,251,681 B2
(45) Date of Patent: Apr. 9, 2019

(54) SYSTEMS AND METHODS FOR PERFORMING SPINAL SURGERY

(71) Applicant: SPINELOOP, LLC, Newport Beach, CA (US)

(72) Inventors: Ashraf Taha, Irvine, CA (US); Marc Greeley, Newport Beach, CA (US); Abdullah Kaki, Jeddah (SA); Eran Levit, Amherst, NH (US)

(73) Assignee: SPINELOOP, LLC, Newport Beach, CA (US)

( * ) Notice: Subject to any disclaimer, the term of this patent is extended or adjusted under 35 U.S.C. 154(b) by 333 days.

(21) Appl. No.: 14/874,965

(22) Filed: Oct. 5, 2015

(65) Prior Publication Data

US 2016/0106481 A1 Apr. 21, 2016

Related U.S. Application Data

(60) Provisional application No. 62/059,599, filed on Oct. 3, 2014.

(51) Int. Cl.
*A61B 17/70* (2006.01)
*A61B 17/88* (2006.01)

(52) U.S. Cl.
CPC ...... *A61B 17/7097* (2013.01); *A61B 17/7098* (2013.01); *A61B 17/8805* (2013.01); *A61B 17/8855* (2013.01); *A61B 17/8858* (2013.01)

(58) Field of Classification Search
CPC ............ A61B 17/7094; A61B 17/8852; A61B 17/7097; A61B 17/8855; A61F 2/4601
See application file for complete search history.

(56) References Cited

U.S. PATENT DOCUMENTS

| | | | |
|---|---|---|---|
| 2004/0098017 A1* | 5/2004 | Saab | A61B 17/8855 606/192 |
| 2006/0100706 A1 | 5/2006 | Shadduck et al. | |
| 2007/0055276 A1* | 3/2007 | Edidin | A61B 17/8855 606/92 |
| 2008/0255624 A1 | 10/2008 | Arcenio et al. | |
| 2010/0262240 A1 | 10/2010 | Chavatte et al. | |

OTHER PUBLICATIONS

International Search Report and Written Opinion for International App No. PCT/US2015/054049, dated Jan. 19, 2016, Authorized Officer: Blaine R. Copenheaver.

* cited by examiner

*Primary Examiner* — Andrew Yang
(74) *Attorney, Agent, or Firm* — One LLP

(57) ABSTRACT

A system and method for percutaneous loop kyphoplasty is described. An apparatus for the treatment of a targeted vertebral bone fracture includes a first trocar having a first lumen, a proximal end and a distal end, wherein the distal end of the first trocar is configured for surgical insertion into a vertebral body at a first location, a second trocar having a second lumen, a proximal and a distal end, wherein the distal end of the second trocar is configured for surgical insertion into the vertebral body at a second location, a wire tool that is slidable within the first trocar, a grasper tool that is slidable within the second trocar and is configured to temporarily couple to the wire tool within the vertebral body, and a non-deployable balloon that is advanced through the first or second trocar into the vertebral body to facilitate expansion within the vertebral body.

8 Claims, 13 Drawing Sheets

SYSTEMS AND METHODS FOR PERFORMING SPINAL SURGERY

CROSS-REFERENCE TO RELATED APPLICATIONS

This application claims the benefit of and priority to U.S. Provisional Patent Application Ser. No. 62/059,599 filed on Oct. 3, 2014, the contents of which are incorporated herein by reference.

TECHNICAL FIELD

The disclosed embodiments relate generally to performing spinal surgery, and more particularly to performing a kyphoplasty by using a loop approach to access the inner vertebral structure, for example, trabecular bone.

BACKGROUND

Traditional Balloon kyphoplasty is a minimally invasive treatment that is used to relieve pain in patients that have vertebral body fractures or vertebral compression fractions caused by osteoporosis, cancer, or benign lesions. During traditional kyphoplasty, one or two independent balloons are used to create a cavity in the trabecular bone and restore vertebral body height, thereby allowing orthopedic cement to be injected to and stabilize the fracture.

The traditional kyphoplasty has been a successful tool for practitioners to help relieve pain for patients with kyphosis and vertebral body fractures. Several failures during traditional kyphoplasty have plagued practitioners, however. They include, for example, issues of iatrogenic cortical rim fracture created during inflation of balloon at the vertebral endplates. This complication is caused because standard kyphoplasty balloon is only controlled from the proximal end nearest the surgeon. The distal end of the standard kyphoplasty balloon is not controlled. During inflation, equal distribution of pressure of the balloon places the distal tip of standard kyphoplasty balloon in places unintended by the practitioner. Other predisposing factors for vertebral cortical fracture may be the presence of heterogeneous bone structures affecting balloon placement. This can lead to nonuniform balloon expansion during traditional unipedicle or bipedicle balloon kyphoplasty leading to subsequent cortical rim fracture. Thus, there exists a need to improve the kyphoplasty surgery that allows the practitioner to have full control and maneuverability of the kyphoplasty balloon from both a proximal and distal end, thereby allowing for the controlled expansion of the balloon as a precursor to cement placement.

BRIEF SUMMARY OF EMBODIMENTS

By way of example and not limitation, one aspect of an apparatus for the surgical treatment of a vertebral bone fracture is disclosed. The apparatus for the treatment of a targeted vertebral bone fracture includes a first trocar having a first lumen, a proximal end and a distal end, wherein the distal end of the first trocar is configured for surgical insertion into a vertebral body at a first location, a second trocar having a second lumen, a proximal and a distal end, wherein the distal end of the second trocar is configured for surgical insertion into the vertebral body at a second location, a wire tool that is slidable within the first trocar, a grasper tool that is slidable within the second trocar and is configured to temporarily couple to the wire tool within the vertebral body, and a non-deployable balloon that is advanced through the first or second trocar into the vertebral body to facilitate expansion within the vertebral body.

In another aspect of the disclosure, an apparatus for the surgical treatment of a vertebral bone fracture with a deployable stent is also disclosed. An apparatus for the treatment of a targeted vertebral bone fracture includes a first trocar having a first lumen, a proximal end and a distal end, wherein the distal end of the first trocar is configured for surgical insertion into a vertebral body at a first location, a second trocar having a second lumen, a proximal and a distal end, wherein the distal end of the second trocar is configured for surgical insertion into the vertebral body at a second location, a wire tool that is slidable within the first trocar, a grasper tool that is slidable within the second trocar and is configured to temporarily couple to the wire tool within the vertebral body, and a non-deployable balloon having at least one deployable stent removably coupled to the balloon, wherein the balloon is advanced through the first or second trocar into the vertebral body to facilitate expansion within the vertebral body.

A method for the treatment of a targeted vertebral bone fracture is also disclosed. The method includes entering a first trocar into a vertebral body of the targeted vertebral bone fracture at a first location, entering a second trocar into a vertebral body of the targeted vertebral bone fracture at a second location, introducing a wire tool and advancing it coaxially within the first trocar, introducing a grasper tool and advancing it coaxially within the second trocar, deploying a distal end of the grasper tool to temporarily couple the wire tool and proximally retracting the grasper tool and the wire tool, inserting a non-deployable balloon through the first or second trocar into the vertebral body to facilitate expansion within the vertebral body and subsequently inflating and deflating the balloon so as to expand inside the vertebral body, retracting the balloon, and inserting orthopedic cement into a void created by balloon expansion.

Another method for the treatment of a targeted vertebral bone fracture is also disclosed. The method includes entering a first trocar into a vertebral body of the targeted vertebral bone fracture at a first location, entering a second trocar into a vertebral body of the targeted vertebral bone fracture at a second location, introducing a wire tool and advancing it coaxially within the first trocar, introducing a grasper tool and advancing it coaxially within the second trocar, deploying a distal end of the grasper tool to temporarily couple the wire tool and proximally retracting the grasper tool and the wire tool, inserting a non-deployable balloon having at least one deployable stent removably coupled to the balloon, wherein the balloon is advanced through the first or second trocar into the vertebral body to facilitate expansion within the vertebral body, deploying the stent, retracting the balloon, and inserting orthopedic cement into a void created by balloon expansion.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Figure 1:
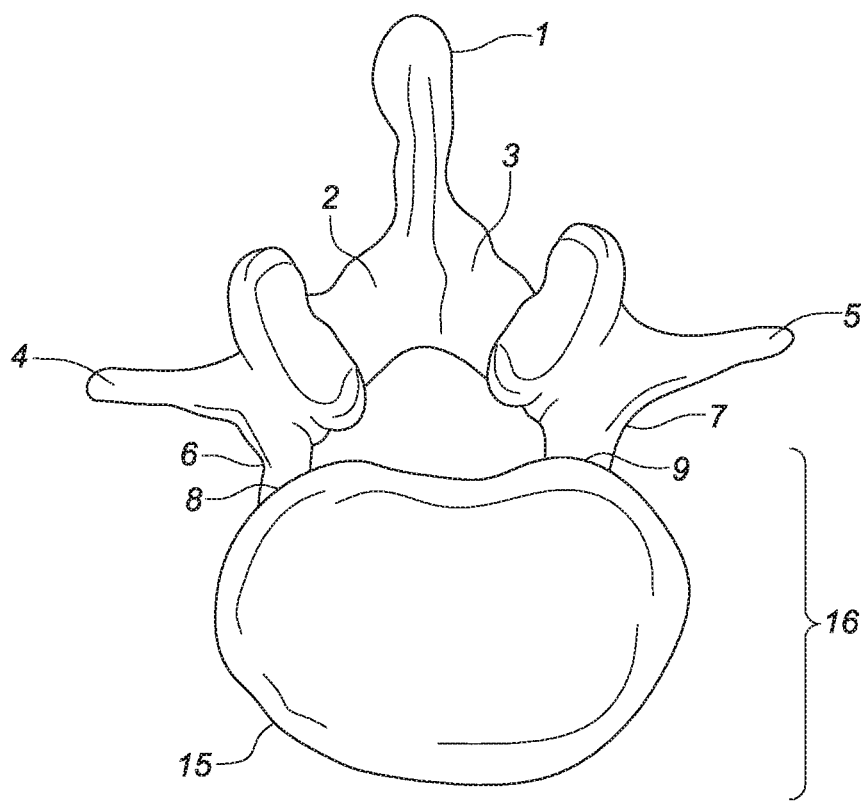
FIG. 1 is an elevated perspective view of a vertebra.

The figures are not intended to be exhaustive or to limit the invention to the precise form disclosed. The figures are not drawn to scale. It should be understood that the disclosed technology can be practiced with modification and alteration, and that the disclosed technology be limited only by the claims and the equivalents thereof.

DETAILED DESCRIPTION OF THE EMBODIMENTS

The technology disclosed herein describes a system that is used to create a loop system from one pedicle to another pedicle on the same vertebra. The loop system can be one or a plurality of loops and can be used to allow to push or pull medical balloons, cement pumps or other medical devices that may be used for medical and surgical purposes including balloon kyphoplasty. The bipedicle loop kyphoplasty described herein may allow for increased surface area and height reduction while preventing any chance of cortical rim iatrogenic fracture. Using a conforming balloon that will adapt to predetermined size and height will allow the practitioner to place cement once the balloon has been deflated. The larger size cavity formed from the loop kyphoplasty system may help prevent maximal height loss. The balloon being placed and controlled by both proximal and distal end may prevent straightening of the balloon and prevent vertebral endplate damage, adjacent vertebral damage and ultimately cement leakage.

As any person of ordinary skill in the art may appreciate, a practitioner may begin by choosing the target vertebra which the patient requires reduction for compression or wedge vertebral body fractures. The practitioner then proceeds to place the patient in a position where he or she may be able to enter trocars through both pedicles. Next, a tool with grasping mechanism and ability to be seen under fluoroscopy may be introduced. The tool may have potential for endoscope capabilities from one trocar. Correspondingly, a separate tool may be introduced to receive the grasping mechanism in the form of a guidewire type tool. The guidewire type tool may be positioned under fluoroscopy and or endoscopy and form a union between the grasper tool and the guide wire tool. Once this union is formed in the body of the vertebra, the tools are pulled out from either trocar, thereby creating a loop in the body of the vertebra and subsequently allowing the practitioner to be able to pull in tools such as balloons or other medical tools.

There are several ways to reduce the fracture of the vertebral body. The first is to use traditional methods following balloon reduction. This includes methods of cement injection. As disclosed herein, a balloon stent system may also be used. The balloon stent system may provide an expanded stent that is opened as the balloon reaches maximum inflation. Once the balloon is inflated, the stent or stents are fully expanded. The balloon is deflated, and the stent(s) maintain the height structure of the newly formed cavity. An additional iteration of this stent system is disclosed by following the newly formed cavity and reduction of the fractured vertebral body, a mechanical stent is pulled into place using the described loop kyphoplasty system that will reduce the fracture and return max height to the vertebral body. Cement may be used to complete the procedures as is readily known in the art.

Additionally, and as also disclosed herein, a porous balloon system may be used as well. This system selectively allows for substances to traverse the balloon membrane into the body of the vertebra allowing for fixation or partial fixation or the reduced fractured vertebral body.

FIG. 1 is an elevated perspective view of a vertebra. FIG. 1 depicts the relevant anatomical structures discussed herein as follows: spinous process 1, left lamina 2, right lamina 3, the left transverse process 4, the right transverse process 5, the left pedicle 6, the right pedicle 7, the junction of where the left pedicle and the body of the vertebra begins on the left side 8, the junction of where the right pedicle and the body of the vertebra begins on the right side 9, the body of the vertebra 16 and the cortical rim 15. As one of ordinary skill in the art may appreciate, the vertebral body 16 consists mainly of cancellous bone, which is soft and has flexible characteristics. Because of these characteristics, the inside of the vertebral body may be manipulated by use of an expanding balloon, much like is done in a traditional kyphoplasty procedure.

Figure 2:
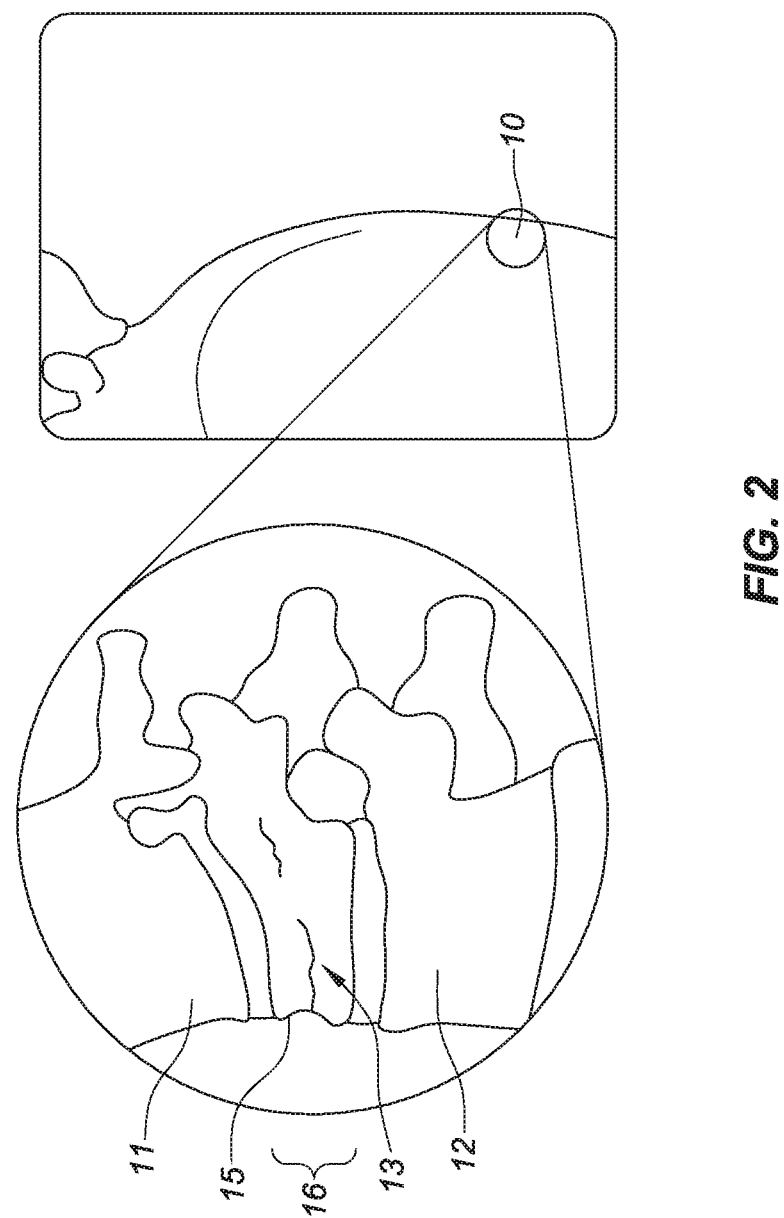
FIG. 2 is a lateral perspective view of a fractured vertebral body.

FIG. 2 is a lateral perspective view of a fractured vertebral body 16. Feature 10 is zoomed in to depict the lumbar area of a patient which correlates to a lumbar vertebral body fracture 13 and the fractured cortical rim 15, with healthy vertebra above and below 11, 12, respectively. A patient suffering from a fractured vertebral body may eventually cause collapse of the entire vertebral body. This condition may cause pain and complications among its sufferers. Although pharmacologic treatments such as NSAIDs and analgesics may be used in acute management of pain, they do not correct the underlying problem causing the pain. Surgically speaking, the goal is decompression of the spinal cord canal and stabilization of the disrupted vertebral column. As depicted in FIG. 2, a patient suffering from a fractured vertebra 16 experiences a collapsed vertebra that may only be corrected by surgery. As disclosed herein, a modified kyphoplasty procedure may reverse the collapsed nature of the vertebra so that the previously collapsed vertebra regains its height and original structure.

Figure 3:
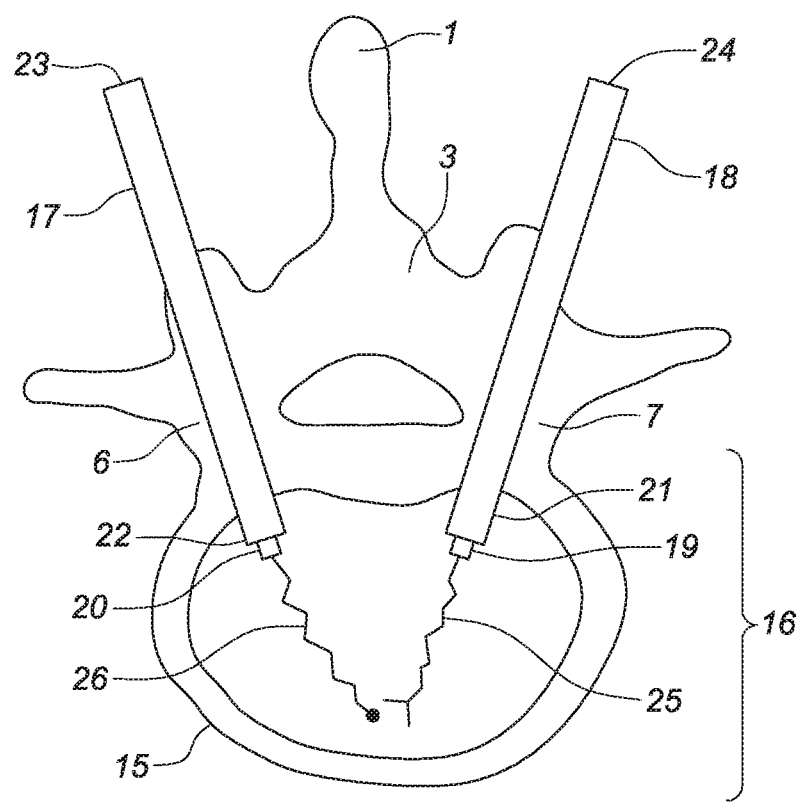
FIG. 3 is an elevated perspective view of a vertebra undergoing loop kyphoplasty.

FIG. 3 is an elevated perspective view of a vertebra undergoing loop kyphoplasty as herein described. The anatomical structure of FIG. 1 has only been slightly modified to reveal a hollow within the vertebral body 16 and a fractured cortical rim 15. As depicted, a left trocar 17 and a right trocar 18 enter the left pedicle 6 and right pedicle 7, respectively. The trocars 17, 18 enter the vertebral body 16 through the pedicle structure on both the left and right sides. Without departing from the teachings herein described, a practitioner can equally choose to access the inner vertebral body through any other access point aside from the left or right pedicles. The left trocar 17 and right trocar 18 may be placed in proper position under guided fluoroscopy (not shown) with the distal end of the left trocar 19 and the distal end of the right trocar 20 shown immediately exiting the junction of the pedicle and the vertebral body 22, 21. The proximal end of the left trocar 23 and the proximal end of the right trocar 24, are seen outside the patient's body (not shown) where medical grade tools may be passed through. By way of non-limiting example, medical grade tools may include a grasper tool 25, guidewire 26, or any other similar tool used to enter the vertebral body 16 through the lumen defined by any trocar. The guidewire tool 26 is seen exiting the left trocar 17. This may be accomplished using guided imagery though not always necessary. Alternatively, in certain circumstances, direct or indirect visualization may be used to receive and capture a tool 25 in an effort to form a loop within the body of the vertebra 16 and extending outside of the patient's body. Once the loop is formed tools such as balloons (not shown) and other medical devices may be pulled into the desired location in the body of the vertebra 16, by using a pulling or pushing technique or catheter over wire technique. Once proper placement of the balloon is accomplished, the practitioner may then expand the balloon while having control of the balloon at both proximal and distal ends. The amount of expansion will necessarily be determined by many factors that the practitioner may take into account, including the level of vertebra being treated, size of the vertebral fracture, and other circumstances.

Figure 4:
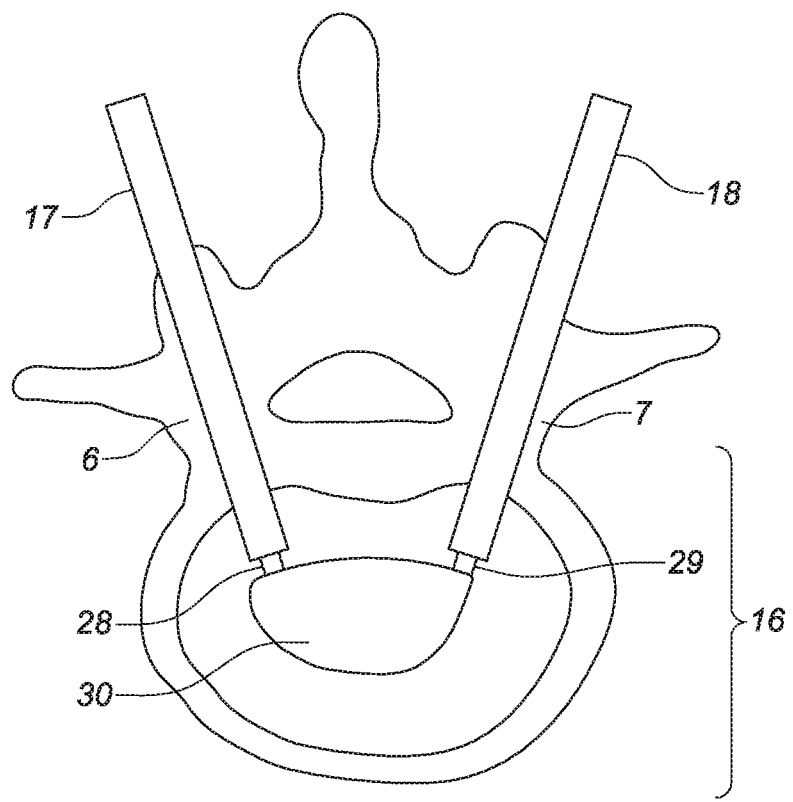
FIG. 4 is an elevated perspective view of a vertebra undergoing loop kyphoplasty depicting an inflated balloon.

FIG. 4 is an elevated perspective view of a vertebra undergoing loop kyphoplasty depicting an inflated balloon. The inflated balloon 30 has already been placed in desired position following the creating of a loop between the left trocar 17 and the right trocar 18 within the body of the vertebra 16 as discussed above. As depicted in FIG. 4, the balloon 30 may be controlled by both sides. The left side of the balloon 28 exits from the left trocar 17 that exits from the left pedicle 6 into the vertebral body 16, and right side of the balloon 29 is controlled from right trocar 18 that exits from the right pedicle 7 into the vertebral body 16. This configuration may give two access ports into the balloon 30 that may allow inflation from two ports as well as controlling the direction of expansion. This is desirable since balloons under high pressure typically move in the direction of least resistance, and, by use of the teachings described herein, the loop kyphoplasty technique keeps the balloon 30 at desired location.

Figure 5:
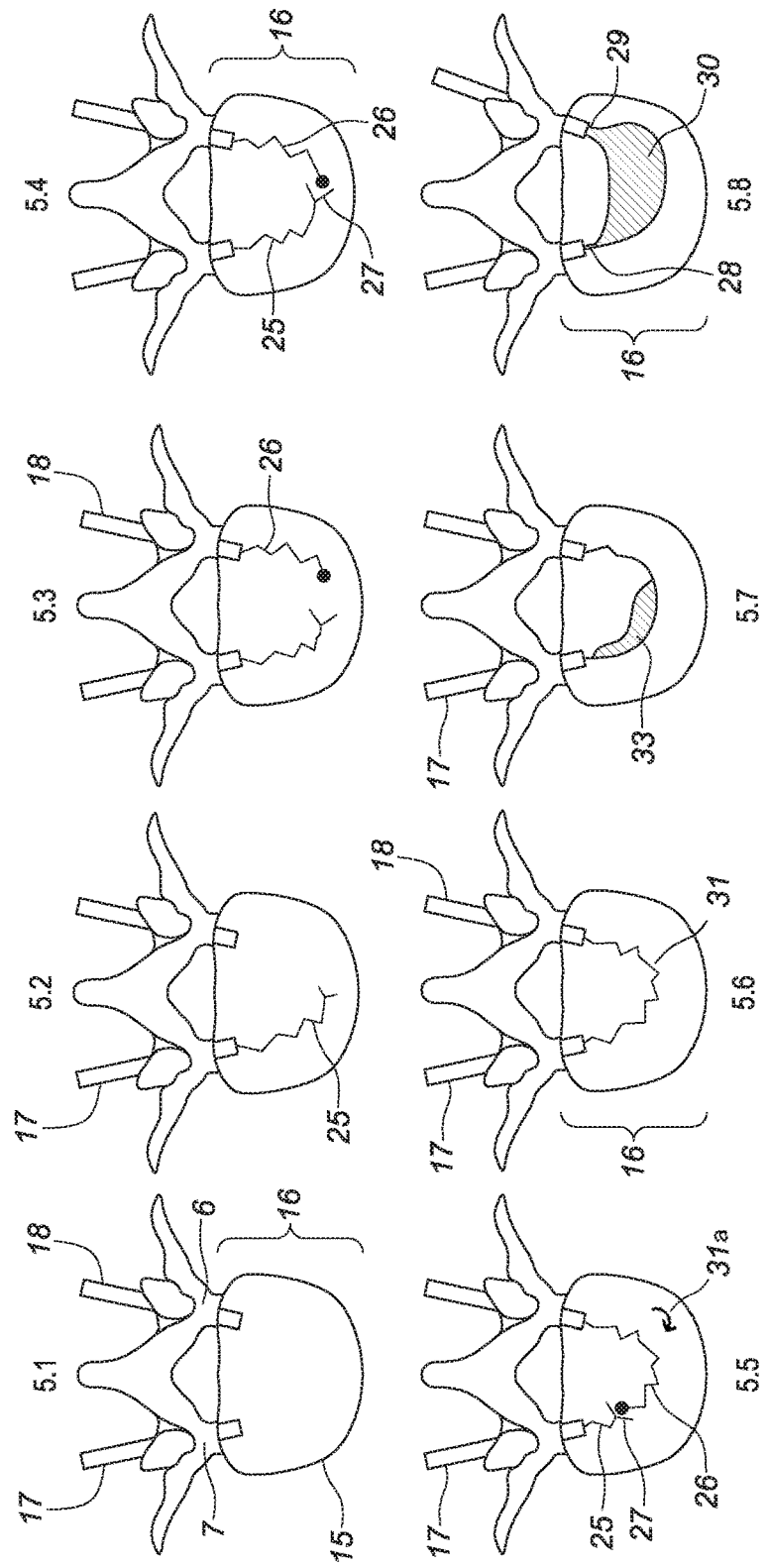
FIG. 5 is a progressive timeline representation of loop kyphoplasty, depicting multiple elevated perspective views of a vertebral body undergoing a kyphoplasty procedure.

FIG. 5 is a progressive timeline representation of a loop kyphoplasty procedure depicting multiple elevated perspective views of a vertebral body undergoing a kyphoplasty procedure. Unlike its traditional counterpart, loop kyphoplasty may only require one balloon for adequate treatment. The following description demonstrates how using a bipedicle two trocar system, loop kyphoplasty can be performed by forming a union between a guidewire and grasper tool. Once the union is formed, tools such as balloons and cement injectors may be placed at a desired location inside the vertebral body 16.

At FIG. 5.1, a vertebra with a left trocar 17 exits the left pedicle 7 and enters the vertebral body 16. A right trocar 18 exits the right pedicle 6 and enters the vertebral body 16. The outer layer of the vertebral body 16 is represented by the fractured cortical rim 15. At FIG. 5.2, once access to the hollow within the vertebral body 16 is achieved, a grasper tool 25 exits the left or right trocar 17 and enters the hollow. At FIG. 5.3, a guidewire tool 26 exits the right or left trocar 18, depending on which lumen remains accessible. At FIG. 5.4, a union 27 is formed between the guidewire tool 26 and grasper tool 25 within the vertebral body 16, thus, forming a loop. Once this loop is created, it provides a mechanism where the practitioner is able to pass tools from outside the body, through the left and/or right trocars into the body of the vertebra 16. This loop gives the practitioner added control as compared to unidirectional wires that only have control at the proximal end. This kypholoop arrangement provides control at both the proximal and distal ends of the wire and provides an outlet from outside the patient's body into the body of the vertebra 16. At FIG. 5.5, union 27 of the grasper tool 25 and the guide wire tool 26 are depicted as being pulled into and out of the left trocar 17. Arrow 31a represents direction guide wire tool 26 is moving towards. It should be obvious to one of ordinary skill that any direction ascribed to the processes described herein can just as readily be reversed without departing from the teaching disclosed.

At FIG. 5.6, loop 31, which is now formed in the body of the vertebra 16, connects the bipedicle trocar system 17, 18 which may allow tools and medical devices to be pulled into place by either pulling or pushing the tools attached to the loop 31 or by catheter over wire technique. In one exemplary embodiment, a balloon may be used as one of the aforementioned tools and is depicted in FIGS. 5.7 and 5.8. FIG. 5.7 demonstrates the introduction of a deflated balloon 33 exiting the left trocar 17. At FIG. 5.8, an inflated balloon 30 placed in desired position within the vertebral body 16 and is controlled by the practitioner at both left (proximally) 28 and right (distally) 29 sides. Additionally, the inflated balloon 30 may have two points of where inflation may occur 28, 29. The inflated balloon 30 will create a cavity that is able to reduce vertebral body fracture (not seen) in so doing creating a displacement area or hollow that would allow for the introduction of orthopedic cement to be injected in the newly formed cavity that will allow for subsequent reducing of the vertebral bone fracture and alleviating the patient's pain.

Figure 6:
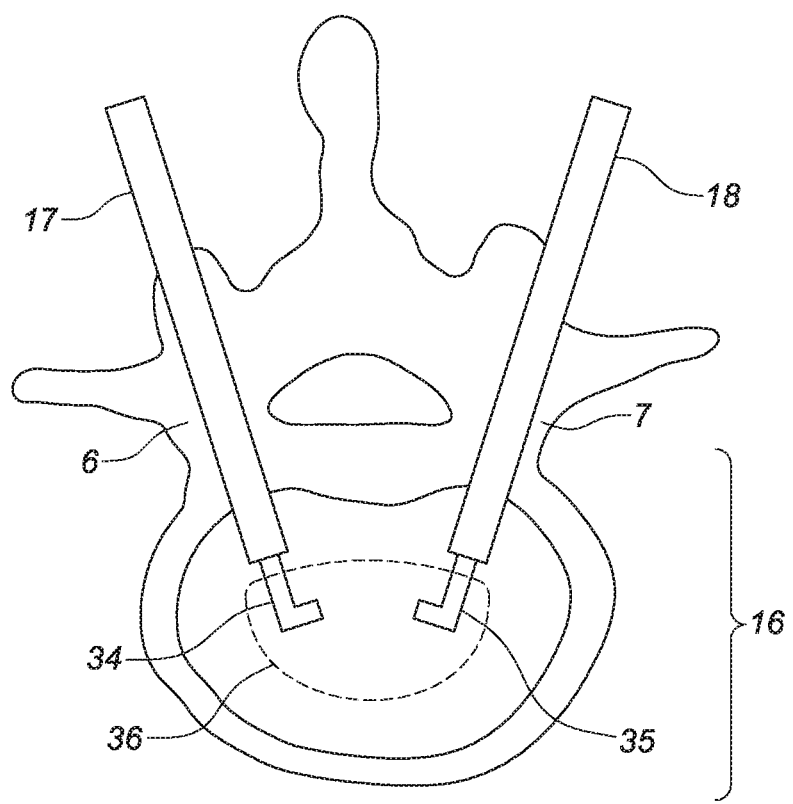
FIG. 6 is an elevated perspective view of a vertebra depicting a right and left cement injector in the newly formed cavity.

FIG. 6 is an elevated perspective view of a vertebra depicting a right and left cement injector disposed within the newly formed cavity. FIG. 6 represents left and right cement injector 34, 35 placed following the formation of the cavity 36 previously described and formed by balloon inflation/deflation and removal, which has reduced the vertebral bone fracture. The left cement injector 34 may be placed in a desired position exiting the left trocar 17 within the newly formed cavity 36. The right cement injector 35 may already have been placed in a desired position exiting the right trocar 18. Again, as depicted in FIG. 6, although the trocars are depicted as entering the vertebral body 16 by way of the left pedicle 6 and right pedicle 7, the teaching disclosed herein are not so limited and access may be achieved from any point around the cortical rim.

Figure 7:
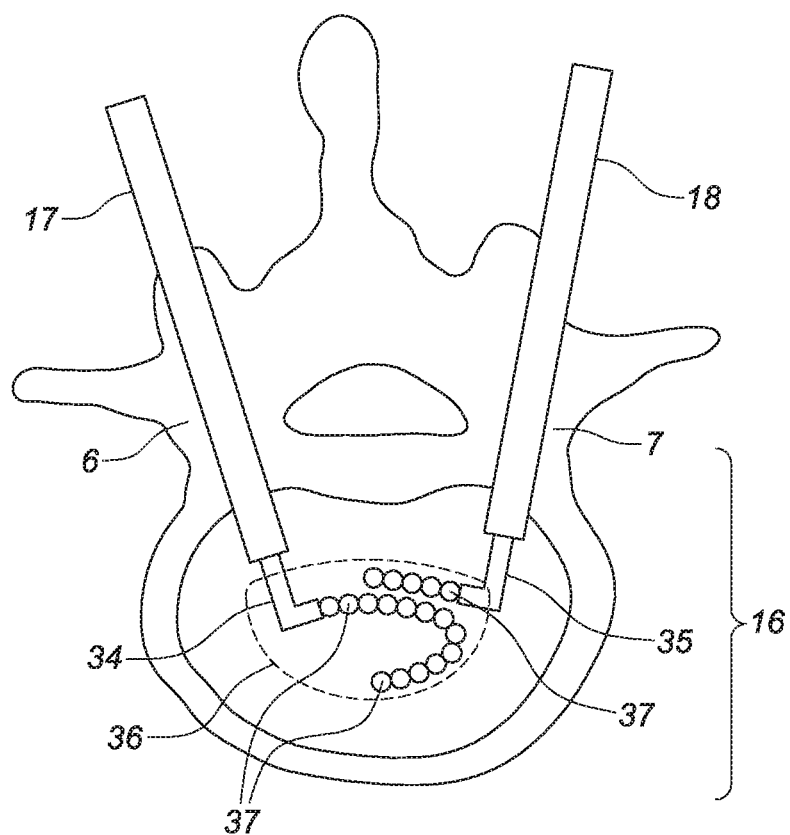
FIG. 7 is an elevated perspective view of right and left cement injectors filling a reduced vertebral body fracture cavity with cement.
Figure 8:
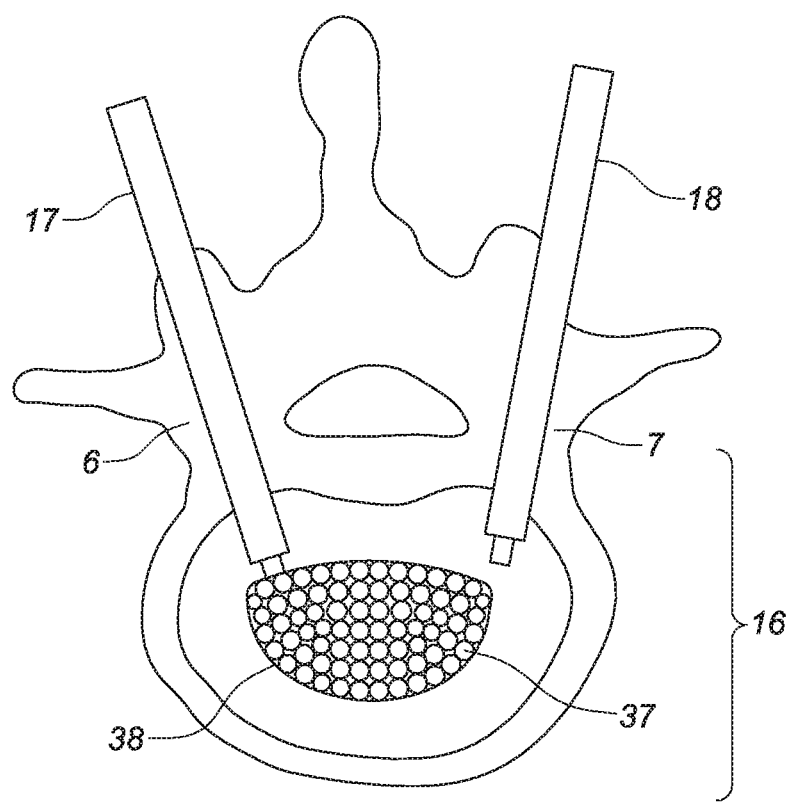
FIG. 8 is an elevated perspective view of a cement filled reduced cavity following removal of right and left cement injector.

FIG. 7 is an elevated perspective view of right and left cement injectors 34, 35 that are depicted as filling a previously reduced vertebral body fracture cavity 36 with cement 37. As previously described, the cavity 36 represents a hollow that was created by inflating the kypholoop balloon. As depicted, the cement 37 may be inserted into the hollow 36 to fill the reduced vertebral bone fracture thereby permanently increasing the height of the vertebra and reducing pain. As a continuation of this process, FIG. 8 is an elevated perspective view of a cement filled reduced cavity following removal of right and left cement injector. The reduced cement filled cavity 38 effectively reduces the fracture of the body of the vertebra 16. The left trocar 17 and the right trocar 18 will be withdrawn once reduced cement filled cavity 38 is formed.

Figure 9:
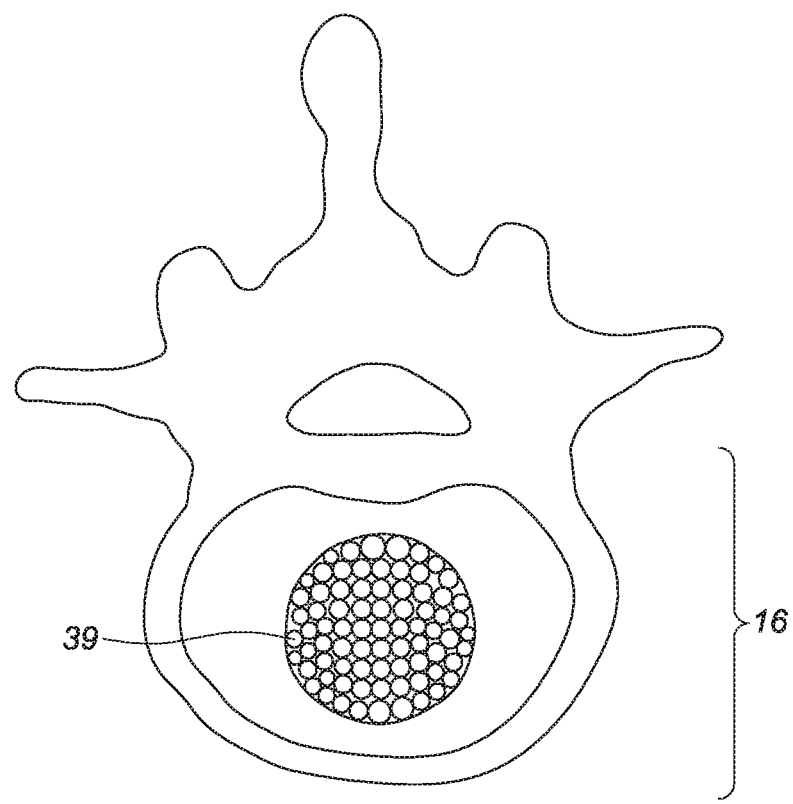
FIG. 9 is an elevated perspective view of a vertebra that has undergone loop kyphoplasty with reduction and cement fixation.

FIG. 9 is an elevated perspective view of a vertebra that has undergone loop kyphoplasty with reduction and cement fixation. The cement circle 39 represents the reduction and cement fixation in the body of the vertebra 16. In other words, once the kyphoplasty treatment is successful, the reduced vertebral body is permanently restored.

Figure 10:
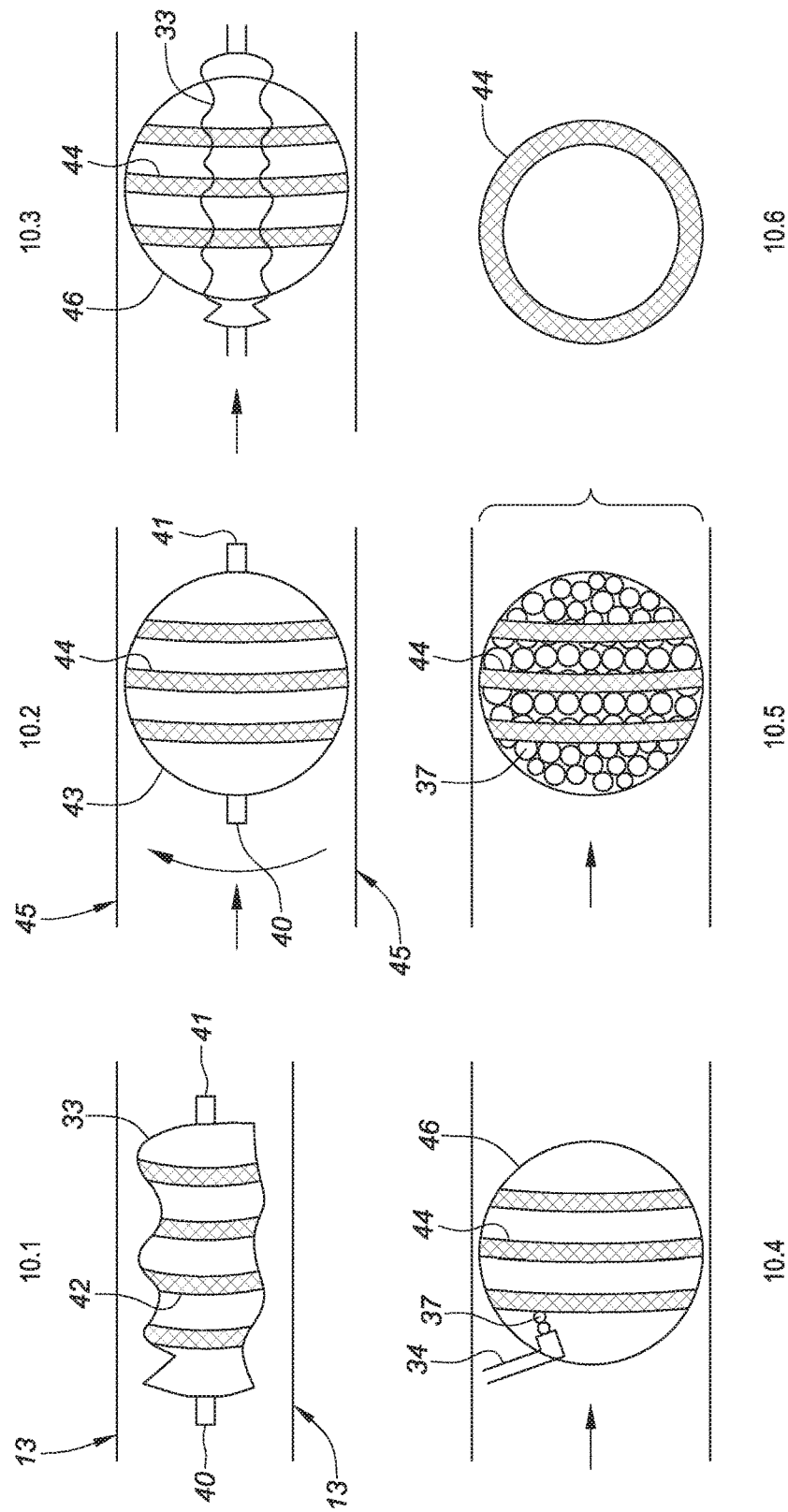
FIG. 10 represents a timeline depicting the steps needed in balloon loop kyphoplasty stent system.

In an alternative embodiment, the loop kyphoplasty procedure previously described may also be facilitated by use of deployable stents or scaffolds that may be used to facilitate the reduction of a fractured vertebral body. FIG. 10 represents a timeline of a balloon loop kyphoplasty stent system using kyphostents. Although there may be other stents used in kyphoplasty, no stents are presently deployed through the loop technique herein described. At FIG. 10.1, a deflated balloon 33 with a proximal end 40 and distal end 41 is wrapped in multiple stents 42. The deflated balloon 33 and collapsed stents 42 are being pulled through and into desired location through the previously described loop kyphoplasty system and into the fractured vertebral body. The left proximal port 40 and right distal port 41 help direct the deflated balloon 33 into a desired location. At FIG. 10.2, an inflated balloon 43 expands the deployable stents 44 to facilitate the reduction of the vertebral body 45. The upward arrow depicts increased height and reduction of the vertebral body fracture. The inflated balloon 43 may be inflated by either the proximal 40 or distal side 41 of the balloon. At FIG. 10.3, a newly formed reduced vertebral body fracture cavity 46 that has been created after balloon inflation is depicted. Following deflation of the balloon 33, the kyphostents 44 remain in an expanded position, maintaining maximum height of the newly formed cavity 46. At FIG. 10.4, the left cement injector 34 is used to inject cement 37 into the newly formed reduced cavity 46 with the kyphostents 44 in place. At FIG. 10.5, a reduced vertebral fracture is shown. The result is a filled maximum height cavity with kyphostent 44 and cement 37 fixation. The advantage of using a kyphostent 44 system eliminates the possibility of maximal height loss following vertebral fracture reduction and balloon deflation. FIG. 10.6 represents a side view of the expanded kyphostent 44.

Figure 11:
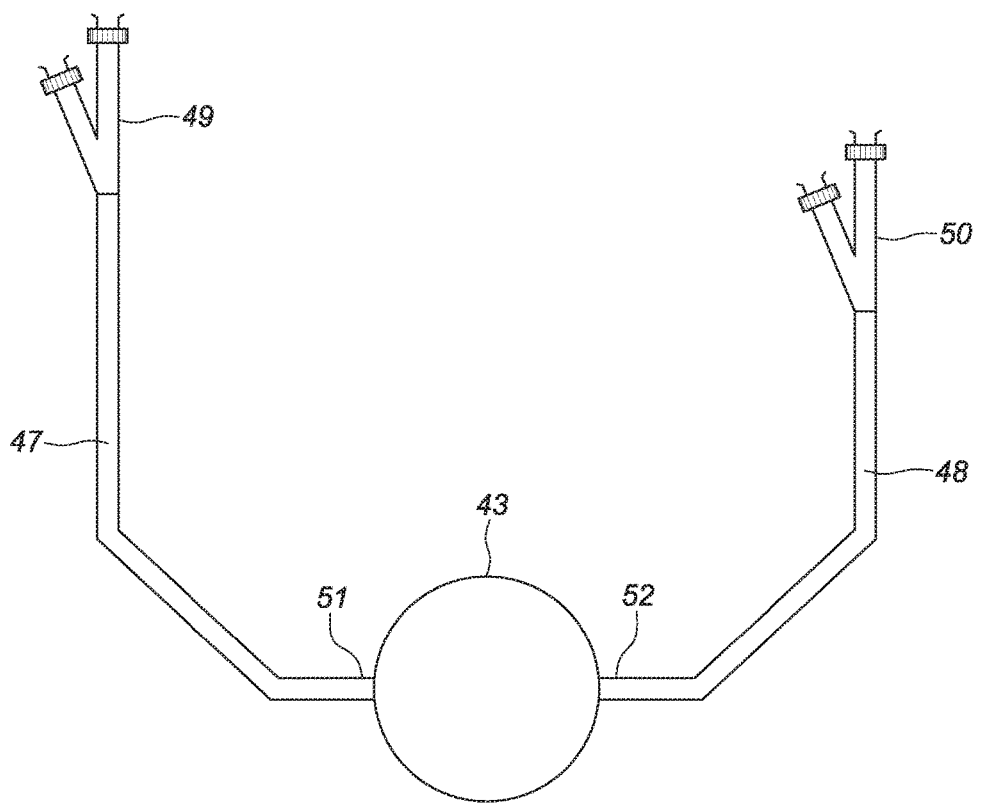
FIG. 11 is an elevated perspective view of a dual channel balloon with two ports of access used in balloon loop kyphoplasty.

FIG. 11 is an elevated perspective view of a dual channel balloon with two ports of access that may be used in a balloon loop kyphoplasty as herein described. The left port 47 and the right port 48 have a left proximal part 49 and right proximal part 50 outside the patient's body and a left distal portion 51 and a right distal portion 52 attached to the respective side of the balloon. Having two ports of access for the loop kyphoplasty inflated balloon 43 may allow for both ports to facilitate balloon expansion from outside the body.

Figure 12:
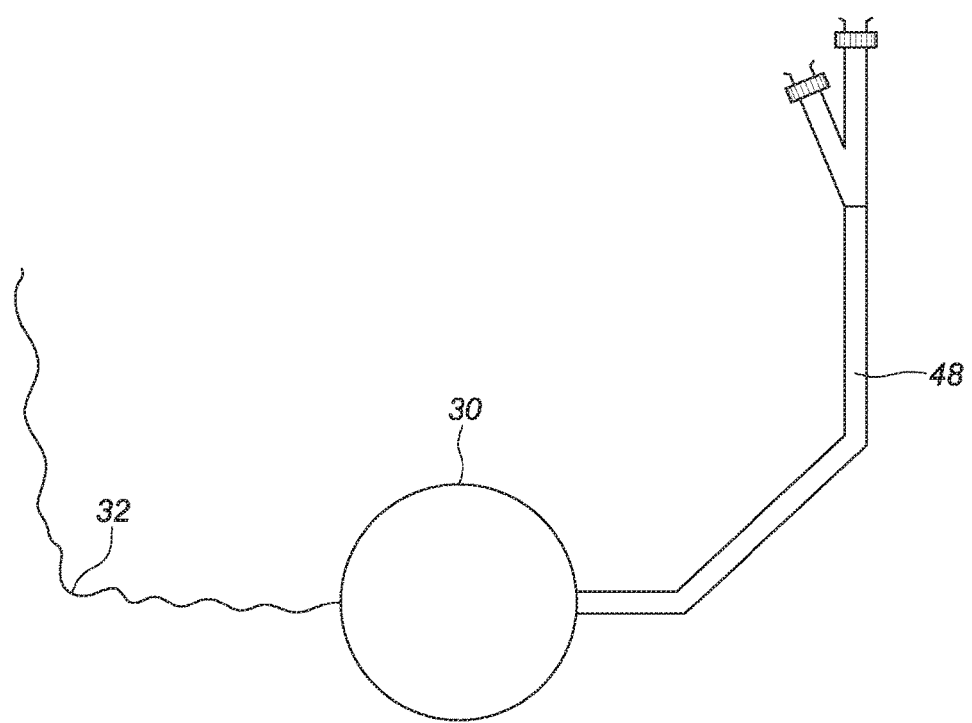
FIG. 12 is an elevated perspective view of a loop kyphoplasty balloon demonstrating proximal and distal control.

FIG. 12 is an elevated perspective view of a loop kyphoplasty balloon demonstrating proximal and distal control. FIG. 12 depicts an inflated balloon 30 with a left-sided wire 32 attachment which may allow desired placement into the body of the vertebra. The wire 32 may provide either proximal or distal control of the balloon depending on which side it is attached to during balloon loop kyphoplasty. Providing distal and proximal control may provide the practitioner with the ability to direct the balloon 30 in a manner that is not otherwise possible. FIG. 12 further depicts a right sided port 48 that inserts into the right side of the inflated balloon 30 which may be used to pass gases and mixtures that will allow for the inflation of the balloon as is common in the art.

As referred to herein, a balloon may be a part of a balloon catheter system. The balloon may be independent of a wire tool or trocar. The balloon catheter system may have a proximal, middle and distal ends. The distal end of the balloon catheter system may be coupled to the wire loop system. The wire loop system may then be pulled proximally from one trocar, thus, subsequently pulling and placing the balloon catheter system into a desired location within the vertebral body. Once in a desired location, the middle portion may be defined as the inflatable balloon. The proximal end of the balloon catheter system may traverse into one trocar system, through the vertebral body, and out the opposite trocar at the same vertebra. Once in place, the balloon catheter system may have two proximal ports 49, 50 outside the body and a middle inflatable portion 43 inside the vertebral body 16.

Figure 13:
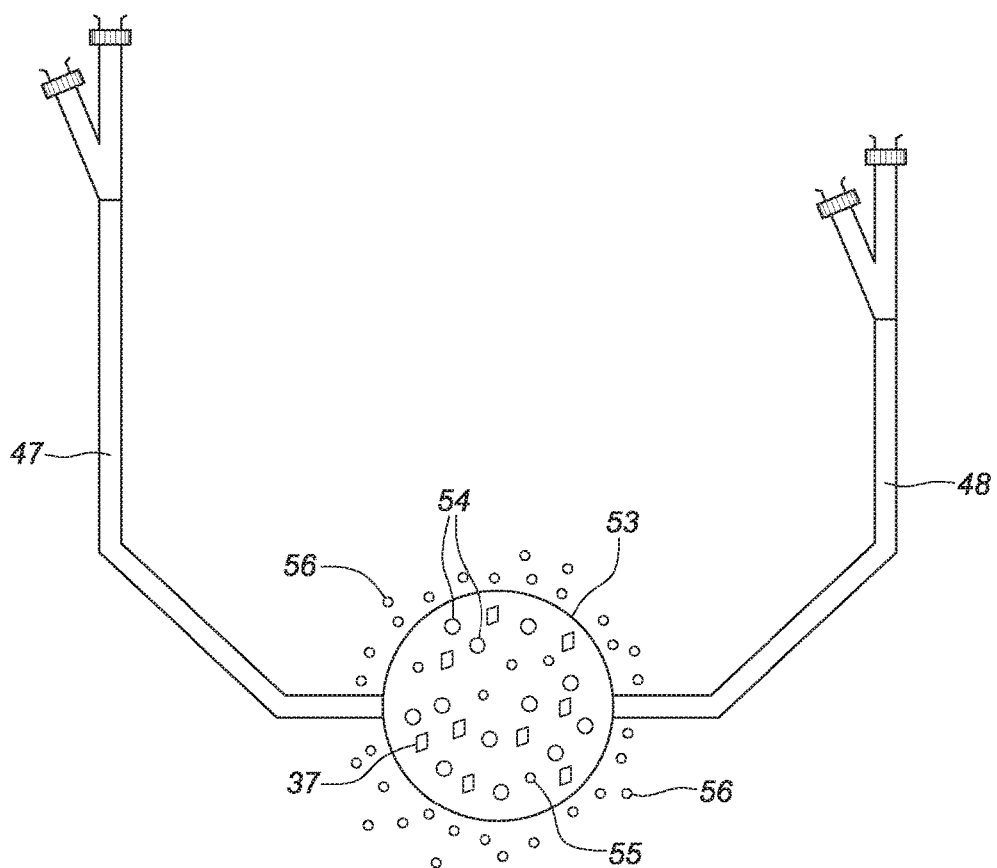
FIG. 13 is an elevated perspective view of a balloon with selective porous membrane.

FIG. 13 is an elevated perspective view of a balloon with selective porous membrane. FIG. 13 depicts a two port porous balloon 53 that allows for the ability of a porous membrane that allows for certain materials to flow out of the balloon while selectively retaining others. In this example, the porous membrane balloon 53 is inflated, the pores 54 represented by hollow circles upon the porous balloon 53 allow for particles that can escape though the pores. The particles that can escape through the pores are represented by black dots inside 55 the porous balloon and black dots outside 56. The black squares 37 inside the balloon represent a particle or particles that cannot exit the pores 54 of the porous balloon 53. Left sided port 47 and right side port 48 have a proximal point that is outside the body and distal point attached to the porous balloon 53. The left side port 47 and right sided port 48 allow for gases, solvents, mixtures, liquids, non organic and organic particles, nanotechnology and polymers to be disbursed into the balloon as part of the aforementioned kyphoplasty surgical embodiments.

While various embodiments of the disclosed technology have been described above, it should be understood that they have been presented by way of example only, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the technology disclosed herein. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A method for the treatment of a targeted vertebral bone fracture, the method comprising the steps of:
    entering a first trocar into a vertebral body of the targeted vertebral bone fracture at a first location;
    entering a second trocar into a vertebral body of the targeted vertebral bone fracture at a second location;
    introducing a wire tool and advancing it coaxially within the first trocar;
    introducing a grasper tool and advancing it coaxially within the second trocar;
    deploying a distal end of the grasper tool to temporarily couple to the wire tool and proximally retracting the grasper tool and the wire tool;
    creating a void within the vertebral body by inserting a balloon through the first or the second trocar into the vertebral body to facilitate expansion within the vertebral body, and subsequently inflating and deflating the balloon so as to create the void within the vertebral body;
    retracting the deflated balloon; and
    inserting orthopedic cement into the void created by balloon expansion.

2. The method of claim 1 wherein the balloon is porous and the method further comprises the step of passing fluids or medicines through the first or second trocar through the balloon for delivery into the vertebral body while the balloon is inflated within the vertebral body.

3. A method for the treatment of a targeted vertebral bone fracture, the method comprising the steps of:
    entering a first trocar into a vertebral body of the targeted vertebral bone fracture at a first location;
    entering a second trocar into a vertebral body of the targeted vertebral bone fracture at a second location;
    introducing a wire tool and advancing it coaxially within the first trocar;
    introducing a grasper tool and advancing it coaxially within the second trocar;
    deploying a distal end of the grasper tool to temporarily couple the wire tool and proximally retracting the grasper tool and the wire tool;
    inserting a balloon having at least one deployable stent removably coupled to the balloon, wherein the balloon is advanced through the first or second trocar into the vertebral body to facilitate expansion within the vertebral body;
    deploying the stent;
    retracting the balloon; and
    inserting orthopedic cement into a void created by balloon expansion.

4. The method of claim 3 wherein the balloon is porous and the method further comprises the step of passing fluids or medicines through the first or second trocar through the balloon for delivery into the vertebral body while the balloon is inflated within the vertebral body.

5. The method of claim 1, wherein the first location is a first pedicular junction and the second location is a second pedicular junction.

6. The method of claim 1, wherein the grasper tool comprises a distal end configured to receive the wire tool by having a pair of grasping forceps, a fork-shaped grasper, a locking device, a pinching door, an adhesive, or a magnet.

7. The method of claim 3, wherein the first location is a first pedicular junction and the second location is a second pedicular junction.

8. The method of claim 3, wherein the grasper tool comprises a distal end configured to receive the wire tool by having a pair of grasping forceps, a fork-shaped grasper, a locking device, a pinching door, an adhesive, or a magnet.

* * * * *